United States Patent
Shelton, IV et al.

(10) Patent No.: US 12,310,583 B2
(45) Date of Patent: May 27, 2025

(54) STAPLE CARTRIDGES COMPRISING TRACE RETENTION FEATURES

(71) Applicant: Cilag GmbH International, Zug (CH)

(72) Inventors: Frederick E. Shelton, IV, Hillsboro, OH (US); Kevin M. Fiebig, Cincinnati, OH (US); Nicholas J. Ross, Franklin, OH (US); Shane R. Adams, Lebanon, OH (US); Sudhir B. Patel, Wesley Chapel, FL (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,831

(22) Filed: Oct. 13, 2023

(65) Prior Publication Data
US 2025/0120708 A1    Apr. 17, 2025

(51) Int. Cl.
*A61B 17/072* (2006.01)
*A61B 17/00* (2006.01)

(52) U.S. Cl.
CPC .. *A61B 17/072* (2013.01); *A61B 2017/00026* (2013.01); *A61B 2017/07271* (2013.01); *A61B 2017/07278* (2013.01); *A61B 2017/07285* (2013.01)

(58) Field of Classification Search
CPC ........ A61B 17/072; A61B 2017/07271; A61B 2017/07278; A61B 2017/07285
See application file for complete search history.

(56) References Cited

U.S. PATENT DOCUMENTS

| | | |
|---|---|---|
| 5,403,312 A | 4/1995 | Yates et al. |
| 5,485,947 A | 1/1996 | Olson et al. |
| 6,978,921 B2 | 12/2005 | Shelton, IV et al. |
| 7,000,818 B2 | 2/2006 | Shelton, IV et al. |
| 7,401,721 B2 | 7/2008 | Holsten et al. |
| 7,407,075 B2 | 8/2008 | Holsten et al. |
| 7,422,139 B2 | 9/2008 | Shelton, IV et al. |
| 7,464,849 B2 | 12/2008 | Shelton, IV et al. |
| 7,669,746 B2 | 3/2010 | Shelton, IV |
| 7,670,334 B2 | 3/2010 | Hueil et al. |
| 7,735,703 B2 | 6/2010 | Morgan et al. |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Food and Drug Administration 510(k) Premarket Notification, https://www.accessdata.fda.gov/scripts/cdrh/cfdocs/cfpmn/pmn.cfm?ID=K182476, last update: Jan. 8, 2024, 1 page.

*Primary Examiner* — Michelle Lopez

(57) ABSTRACT

A staple cartridge comprising a cartridge body including a deck and projections extending from the deck is disclosed. When used with a surgical stapling instrument, the deck of the staple cartridge can be compressed against patient tissue before the staples contained in the staple cartridge are ejected. The projections are engaged with the patient tissue and hold the patient tissue in place. The staple cartridge further comprises an electrical trace defined on the deck that extends between at least two of the projections. The electrical trace is part of a sensor system that detects properties of the patient tissue positioned against the projections.

20 Claims, 6 Drawing Sheets

(56) References Cited

U.S. PATENT DOCUMENTS

| | | |
|---|---|---|
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,499,992 B2 | 8/2013 | Whitman et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,345,481 B2 | 5/2016 | Hall et al. |
| 9,386,988 B2 | 7/2016 | Baxter, III et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,839,420 B2 | 12/2017 | Shelton, IV et al. |
| 9,844,369 B2 | 12/2017 | Huitema et al. |
| 9,924,944 B2 | 3/2018 | Shelton, IV et al. |
| 9,987,008 B2 | 6/2018 | Scirica |
| 10,080,552 B2 | 9/2018 | Nicholas et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,349,939 B2 | 7/2019 | Shelton, IV et al. |
| 10,357,252 B2 | 7/2019 | Harris et al. |
| 10,517,593 B2 | 12/2019 | Gupta et al. |
| 10,537,324 B2 | 1/2020 | Shelton, IV et al. |
| 10,542,981 B2 | 1/2020 | Miller et al. |
| 10,561,419 B2 | 2/2020 | Beardsley |
| 10,568,624 B2 | 2/2020 | Shelton, IV et al. |
| 10,588,623 B2 | 3/2020 | Schmid et al. |
| 10,765,427 B2 | 9/2020 | Shelton, IV et al. |
| 10,898,183 B2 | 1/2021 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,000,278 B2 | 5/2021 | Shelton, Iv et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,291,445 B2 | 4/2022 | Shelton, IV et al. |
| 11,298,129 B2 | 4/2022 | Bakos et al. |
| 11,337,693 B2 | 5/2022 | Hess et al. |
| 11,364,029 B2 | 6/2022 | Burbank et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,660,289 B2 * | 5/2023 | Rands ............... A61K 31/4045 514/415 |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,826,047 B2 | 11/2023 | Huang et al. |
| 11,849,944 B2 | 12/2023 | Shelton, IV et al. |
| 11,896,218 B2 | 2/2024 | Bakos et al. |
| 11,974,741 B2 | 5/2024 | Moubarak et al. |
| 2007/0175955 A1 | 8/2007 | Shelton et al. |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2018/0132849 A1 | 5/2018 | Miller et al. |
| 2018/0168615 A1 | 6/2018 | Shelton, IV et al. |
| 2019/0105047 A1 | 4/2019 | Nalagatla et al. |
| 2021/0196270 A1* | 7/2021 | Shelton, IV ........... G16H 20/40 |
| 2022/0031320 A1 | 2/2022 | Hall et al. |
| 2022/0047256 A1 | 2/2022 | Miller et al. |
| 2022/0047265 A1 | 2/2022 | Miller et al. |
| 2022/0273292 A1* | 9/2022 | Shelton, IV .......... H02J 50/402 |
| 2022/0304679 A1 | 9/2022 | Bakos et al. |
| 2022/0304680 A1 | 9/2022 | Shelton, IV et al. |
| 2022/0346858 A1 | 11/2022 | Aronhalt et al. |
| 2023/0119119 A1 | 4/2023 | Moubarak |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |

\* cited by examiner

STAPLE CARTRIDGES COMPRISING TRACE RETENTION FEATURES

BACKGROUND

The present invention relates to surgical staple cartridges configured for use with surgical stapling instruments designed to staple and cut tissue.

SUMMARY

A staple cartridge comprising a cartridge body including a deck and projections extending from the deck is disclosed. When used with a surgical stapling instrument, the deck of the staple cartridge can be compressed against patient tissue before the staples contained in the staple cartridge are ejected. The projections are engaged with the patient tissue and hold the patient tissue in place. The staple cartridge further comprises an electrical trace defined on the deck that extends between and on at least two of the projections. The electrical trace is part of a sensor system that detects properties of the patient tissue positioned against the projections.

LISTING OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
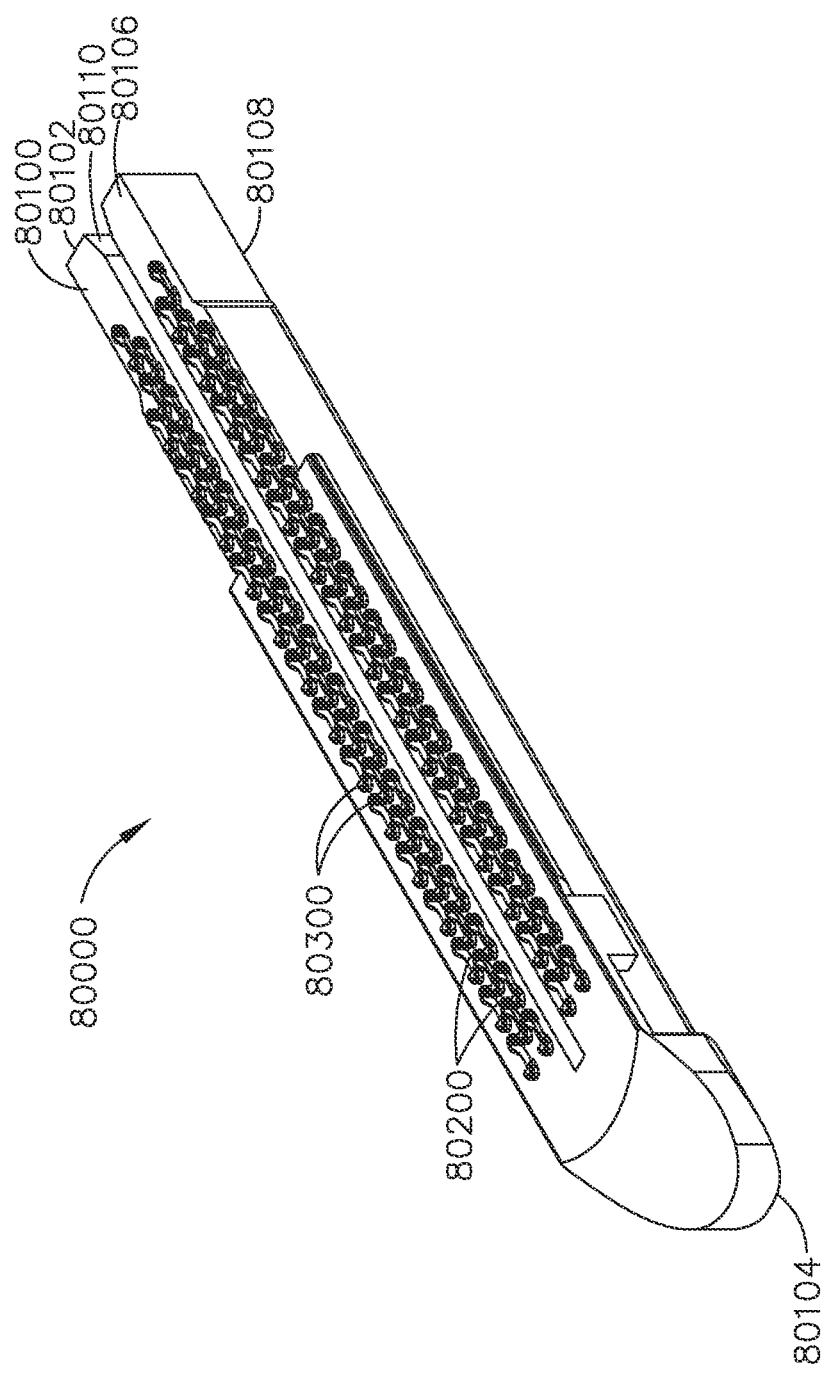
FIG. 1 is a perspective view of a staple cartridge for use with a surgical stapling instrument.

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER;

U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING

ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, a staple cartridge may not be removable from, or at least readily replaceable from, the first jaw. The second jaw comprises an anvil configured to deform staples ejected from the staple cartridge. The second jaw is pivotable relative to the first jaw about a closure axis; however, the first jaw may be pivotable relative to the second jaw. The surgical stapling system further comprises an articulation joint configured to permit the end effector to be rotated, or articulated, relative to the shaft. The end effector is rotatable about an articulation axis extending through the articulation joint. However, the surgical stapling system may not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing driver. The firing driver is configured to contact the sled and push the sled toward the distal end. The longitudinal slot defined in the cartridge body is configured to receive the firing driver. The anvil also includes a slot configured to receive the firing driver. The firing driver further comprises a first cam which engages the first jaw and a second cam which engages the second jaw. As the firing driver is advanced distally, the first cam and the second cam can control the distance, or tissue gap, between the deck of the staple cartridge and the anvil. The firing driver also comprises a knife configured to incise the tissue captured intermediate the staple cartridge and the anvil. It is desirable for the knife to be positioned at least partially proximal to the ramped surfaces such that the staples are ejected ahead of the knife.

Surgical stapling devices are commonly used in a variety of different surgical procedures to staple or otherwise fasten incised tissue. Such devices include an end effector that comprises a pair of jaws that are movable between an open position and closed positions. An elongate shaft is coupled to the end effector that faciliates insertion of the end effector into the patient, oftentimes through a cannula of a trocar or other constricted opening. The shaft may be coupled to a handle, or housing, that facilitates manual actuation of the end effector or the handle may comprise a motor or motors for applying actuation motions to the end effector. In alternative arrangements, the shaft may operably interface with a robotic system which is configured to manipulate the shaft and apply actuation motions to the end effector.

The shaft faciliates the transfer of opening and closing motions to the pair of jaws. A surgical staple cartridge is mounted in one of the jaws that comprises a channel and the other jaw comprises an anvil that is movably supported relative to the channel. The surgical staple cartridge commonly comprises a cartridge body that defines a deck surface that is oriented to face an underside of the anvil. Lines of surgical staples are received on staple drivers that are movably mounted in corresponding staple cavities formed in the cartridge body that open through the deck surface.

The end effector further includes a sled driver, or firing member or firing actuator, that is formed with camming surfaces or is configured to cooperate with a sled that includes camming surfaces or ramps configured to drive the staple drivers upward out of the staple cavities. The sled driver may additionally be provided with other camming members or guide tabs configured to slidably engage the anvil and the channel to retain the anvil at a proper spacing relative to the staple cartridge during the firing process. This spacing between the underside or forming surface of the anvil and the deck of the staple cartridge is often referred to as the "tissue gap." The sled driver in those end effectors that are designed to cut tissue as well as staple or fasten tissue is equipped with a knife, or tissue cutting blade or surface. The shaft accommodates a movable firing beam or other known arrangement configured to drive the sled driver distally through the staple cartridge and retract the sled driver after the cutting and stapling procedure is completed.

The cartridge body is formed with a longitudinal slot that is configured to accommodate travel of the sled driver through the cartridge. The staple cavities open through the deck surface and are arranged to form an orientation of offset longitudinal rows on each side of the longitudinal slot. The staple cavities movably store staples therein. In use, the end effector is positioned adjacent the tissue to be cut and stapled ("target tissue") with the jaws in the open position to enable the target tissue to be positioned between the underside of the anvil and the cartridge deck. The anvil can be moved toward the channel and/or the channel can be moved toward the anvil to motivate the end effector into the closed position. Once the target tissue has been desirably positioned between the anvil and the staple cartridge, the end effector is moved to a fully-closed position thereby clamping the target tissue between the anvil and the cartridge. Thereafter, the firing beam, firing bar, or other actuator arrangement is actuated to advance the sled driver and the sled distally through the cartridge. As the sled moves distally, the camming surfaces thereon sequentially cam the staple drivers upward in the staple cavities causing the staples temporarily supported on the staple drivers to pass through the clamped tissue and into forming contact with the underside of the anvil. The knife or cutting blade of the sled driver lags behind the sled, ensuring that the lines of staples are formed before the clamped tissue is incised.

The operation of surgical instruments during a surgical procedure can be optimized by gathering data during the surgical procedure. Information, or data, can be gathered during the surgical procedure using sensors strategically placed on the surgical instrument. Sensors positioned on and/or near the end effector can provide valuable information to an operating system of the surgical instrument and/or the user of the surgical instrument that can be used to optimize the operation of the surgical instrument and/or the outcome of the surgical procedure, for example. Such sensors can be used to detect various information including, for example, the presence of tissue between jaws of the end effector, a thickness of such tissue, and/or the presence of a foreign object between the jaws of the end effector. An operating system of the surgical instrument can use the detected information to modify an instrument operating parameter, such as a speed of a firing stroke, for example.

Not only can such sensors be used to detect a presence of adjacent articles, such sensors can also be used to detect a status of the end effector. Sensors can be used to determine if a staple has left a particular staple cavity during a staple firing stroke. Detecting the staple leaving its associated staple cavity allows the surgical instrument and/or the user of the surgical instrument to identify a current stage of the staple firing stroke and/or if a staple firing stroke resulted in a successful staple formation, for example. Additional benefits associated with surgical instrument sensors is described in greater detail herein.

FIG. 1 depicts a staple cartridge 85000 for replaceable seating in a cartridge jaw of an end effector. The staple cartridge 85000 comprises a deck surface 85010 configured to oppose an anvil of the end effector when the staple cartridge 85000 is seated in the cartridge jaw. Staple cavities 85100, 85200, 85300 are defined in the staple cartridge 85000 and comprise staples movably stored therein. The staple cavities 85100, 85200, 85300 are arranged in six longitudinal rows, with three longitudinal rows on each side of a longitudinal slot 85005. The longitudinal rows of staple cavities extend between a proximal end 85002 and a distal end 85004 of the staple cartridge 85000. A first longitudinal row of staple cavities extends alongside a second longitudinal row of staple cavities on a first side of the longitudinal slot 85005. A third longitudinal row of staple cavities extends alongside the second longitudinal row of staple cavities on the first side of the longitudinal slot 85005. Staple cavities 85100 in the first longitudinal row are longitudinally-aligned with staple cavities 85300 in the third longitudinal row, while staple cavities 85200 from the second longitudinal row are longitudinally-offset from the staple cavities 85100, 85300 in the first and third longitudinal rows, respectively. While FIG. 1 depicts six longitudinal rows of staple cavities defined in the staple cartridge 85000, any suitable number of staple cavity rows and/or staple cavities is envisioned and can be selected based on a particular surgical procedure, for example.

The longitudinal slot 85005 extends between the proximal end 85002 and the distal end 85004 of the staple cartridge 85000 and is sized to receive a sled driver, or firing actuator, to eject staples out of the staple cartridge 85000 during a staple firing stroke. Various aspects of staple cartridges are described in greater detail in U.S. Pat. No. 9,844,369, the disclosure of which is herein incorporated by reference in its entirety.

Figure 2:
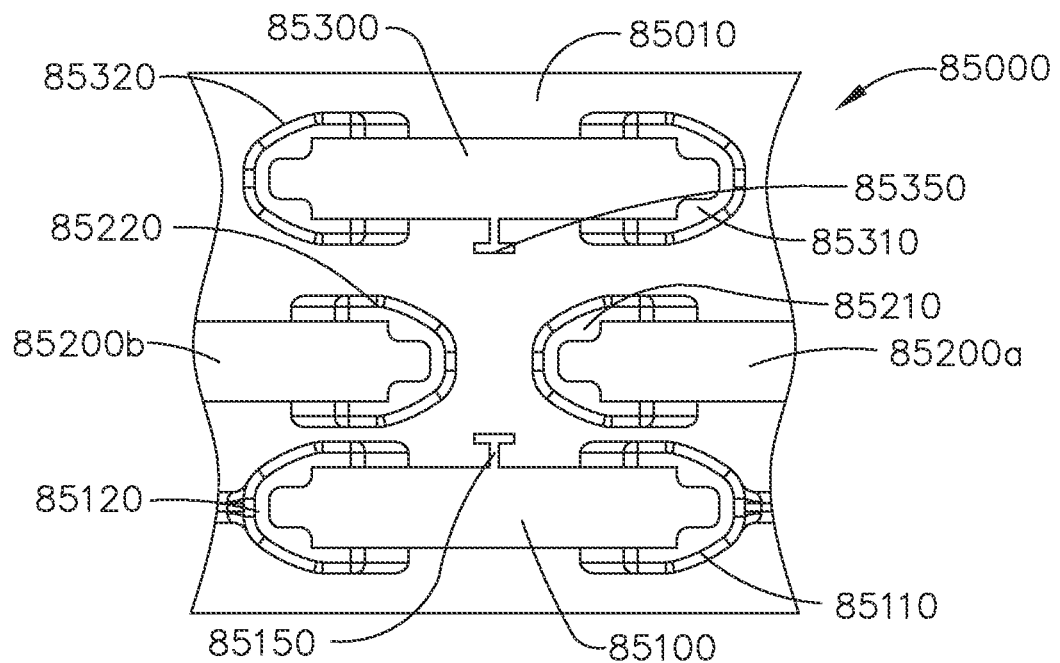
FIG. 2 is a partial plan view of a deck surface comprising trace retention features of the staple cartridge of FIG. 1.

Referring now to FIG. 2, the staple cartridge 85000 further comprises projections extending from the deck surface 85010. The projections are integrated, or integrally-formed, with the staple cartridge 85000 and extend away from the deck surface 85010. Multiple, discrete projections surround at least a portion of the staple cavities defined in the staple cartridge 85000. A first projection 85110 surrounds a proximal portion of a staple cavity 85100 in the first longitudinal row of staple cavities. A second projection 85120 surrounds a distal portion of the staple cavity 85100 from the first longitudinal row. A third projection 85210 surrounds a distal portion of a first staple cavity 85200*a* from the second longitudinal row of staple cavities, and a fourth projection 85220 surrounds a proximal portion of a second staple cavity 85200*b* from the second longitudinal row. A fifth projection 85310 surrounds a proximal portion of a staple cavity 85300 from the third longitudinal row of staple cavities, and a sixth projection 85320 surrounds a distal portion of the staple cavity 85300 from the third longitudinal row.

One or more of the projections of the staple cartridge 85000 extend a staple cavity above the deck surface 85010. For instance, the first projection 85110 and the second projection 85120 extend the staple cavity 85100 above the deck surface 85010. As the staple stored in the staple cavity 85100 is ejected, or fired, during a staple firing actuation, the legs of the staple are supported by the projections 85110 and 85120 when the staple legs emerge above the deck surface 85010. As such, the possibility of the staple legs becoming misaligned with the staple forming pockets defined in the anvil is reduced. Projections 85210, 85220, 85310, and 85320 also comprise staple cavity extenders.

The projections extending from the deck surface 85010 define a valley, or recess, therebetween at least due to the longitudinally-offset orientation of the staple cavities 85200 in the second longitudinal row with respect to the staple cavities 85100, 85300 in the first and third longitudinal rows. The valley defines a continuous pathway extending between the staple cavities 85100, 85200, 85300 and their associated projections.

Figure 3:
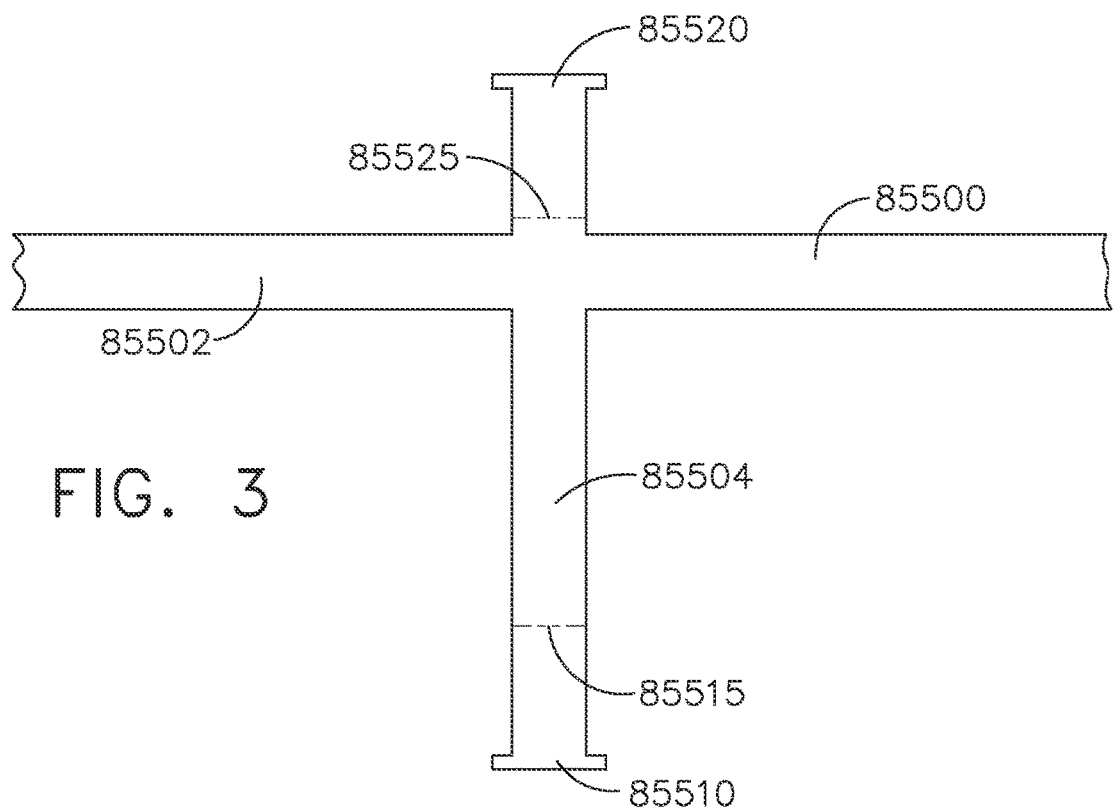
FIG. 3 is a partial plan view of a flexible circuit.

As discussed above, gathering and/or monitoring data during a surgical procedure is often desirable to optimize an operation and/or result of a surgical instrument. Such data can be gathered utilizing a sensor, or other suitable electrical traces capable of conducting signals. The sensor can be positioned on the deck surface 85010 of the staple cartridge 85000 to detect data related to the staple cartridge 85000. Such data can include, for example, whether tissue is positioned adjacent the deck surface 85010 and/or a firing status of the staple cartridge 85000. A sensing array comprising one or more sensors can be integrated with a flexible substrate to form a flexible circuit 85500, as shown in FIG. 3 and shown coupled to the staple cartridge 85000 in FIG. 4. The valley defined amongst the staple cavities and projections on the deck surface 85010 provides an ideal, continuous pathway for a sensing array to extend.

The continuous pathway can be elevated, or stepped, with respect to the deck surface 85010. Stated another way, areas of the staple cartridge 85000 along the path of the flexible circuit 85500 extend above the primary deck surface 85010 to a first height. While such first height is greater than zero (i.e., the height of the primary deck surface 85010), it is less than or equal to a height to which the projections extend from the primary deck surface 85010. Such an elevated pathway allows for the sensing array to achieve a better contact with an adjacent tissue and/or adjunct material than if such a pathway was the same height of the primary deck surface 85010, for example.

The flexible circuit 85500 comprises a first portion 85502 configured to extend longitudinally along a deck surface of a staple cartridge. Stated another way, the first portion 85502 is configured to extend along the deck surface in between two longitudinal rows of staple cavities, such as in between the first longitudinal row and the second longitudinal row or in between the second longitudinal row and the third longitudinal row, for example. Such longitudinal extension of the flexible circuit 85500 allows for the positioning of sensors between longitudinal rows of staple cavities as well as allowing the flexible circuit 85500 to detect information regarding an adjacent article at various longitudinal positions of the staple cartridge 85000. The first portion 85502 can be configured to extend along the deck surface in between the first longitudinal row of staple cavities and the longitudinal slot 85005. The first portion 85502 can be configured to extend along the deck surface in between the third longitudinal row of staple cavities and an outer edge of the staple cartridge 85000.

The flexible circuit 85500 further comprises a second portion 85504 configured to extend laterally along the deck surface. Stated another way, the second portion 85504 is configured to extend along the deck surface in between a staple cavity 85100 from the first longitudinal row and a longitudinally-aligned staple cavity 85300 from the third longitudinal row. Ends 85510 of the second portion 85504 of the flexible circuit 85500 terminate in a T-shape; however, any suitable geometry is envisioned. Such lateral extension of the flexible circuit 85500 allows for the positioning of sensors in between adjacent staple pockets within the same longitudinal row.

Referring back to FIG. 2, a first T-shaped relief 85150 is defined in the staple cartridge 85000. Such first T-shaped relief 85150 extends into a staple cavity 85100 in the first longitudinal row of staple cavities. The first T-shaped relief 85150 is sized and shaped to receive a first end 85510 of the second portion 85504 of the flexible circuit 85500 to secure the flexible circuit 85500 in a desired orientation against the deck surface 85010. A second T-shaped relief 85350 is defined in the staple cartridge 85000 and extends into a staple cavity 85300 in the third longitudinal row of staple cavities. The second T-shaped relief 85350 is sized and shaped to receive a second end 85520 of the second portion 85504 of the flexible circuit 85500 to secure the flexible circuit 85500 in a desired orientation against the deck surface 85010. The first T-shaped relief 85150 is longitudinally-aligned with the second T-shaped relief 85350.

Figure 4:
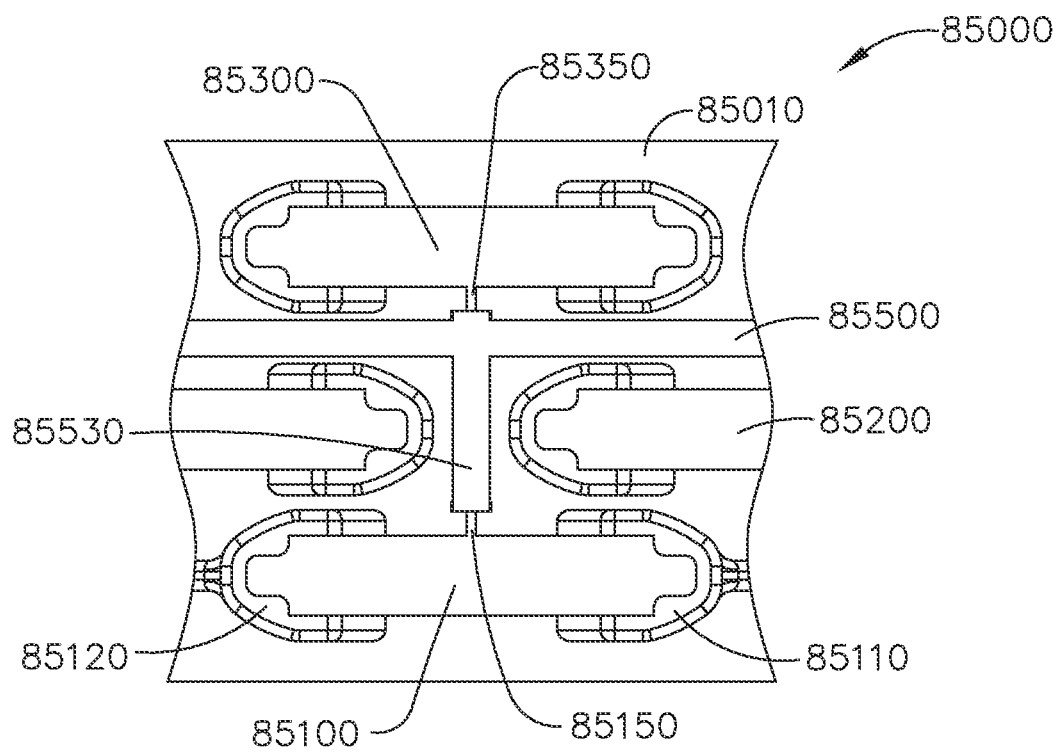
FIG. 4 is a partial plan view of the deck surface of FIG. 2 comprising the flexible circuit of FIG. 3 secured there against.
Figure 5:
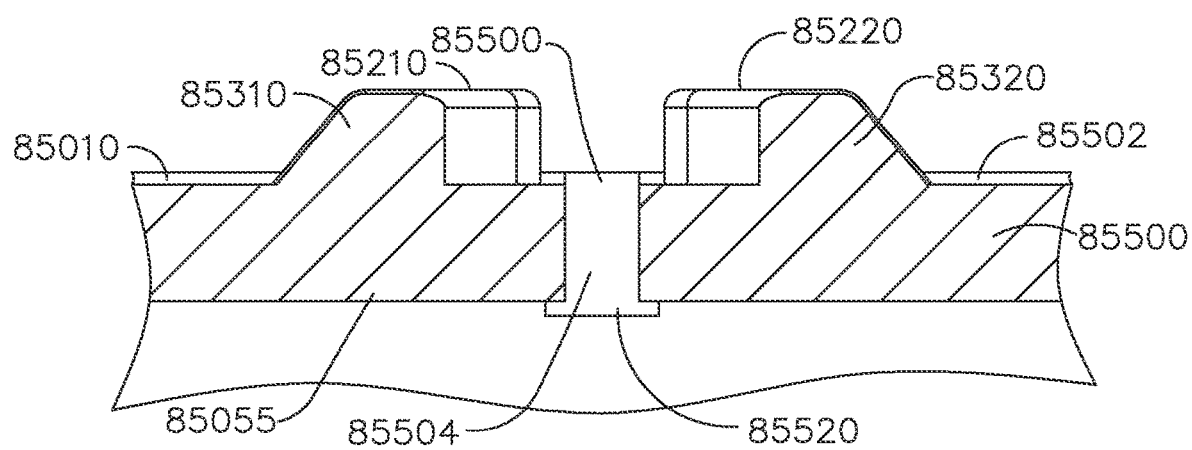
FIG. 5 is a partial cross-sectional view of the deck surface and the flexible circuit of FIG. 4.

In attaching the flexible circuit 85500 to the staple cartridge 85000 as shown in FIGS. 4 and 5, a first end 85510 of the second portion 85504 of the flexible circuit 85500 is aligned with the first T-shaped relief 85150. In order to align the first end 85510 of the second portion 85504 with the first T-shaped relief 85150, the second end 85520 of the second portion 85504 extends in a direction away from the second T-shaped relief 85350. Once the first end 85510 of the second portion 85504 is depressed through the first T-shaped relief 85150, the flexible circuit 85500 is configured to bend and/or fold along a joint 85515. With the first end 85510 of the second portion 85504 depressed into the first T-shaped relief 85150 and the flexible circuit 85500 bent along joint 85515, the second end 85520 of the second portion 85504 extends away from the deck surface 85010 in the same direction as the projections. As the second end 85520 is pulled into alignment with the second T-shaped relief 85350, the first end 85510 engages a shelf 85055 defined in the staple cartridge 85000 and is secured in its desired position. Similarly, the second end 85520 is depressed through the second T-shaped relief 85350. Tension within the flexible circuit 85500 bends and/or folds the flexible circuit 85500 along a joint 85525 thereby engaging the second end 85520 with a shelf 85055 defined in the staple cartridge 85000. Every staple cavity within the first longitudinal row and the third longitudinal row can comprise such a T-shaped relief; however, any frequency of T-shaped reliefs suitable to maintain the flexible circuit 85500 against the deck surface 85010 in its desired position is envisioned. Stated another way, the T-shaped reliefs can be defined in every other staple cavity within the first and third longitudinal rows, for example.

Figure 6:
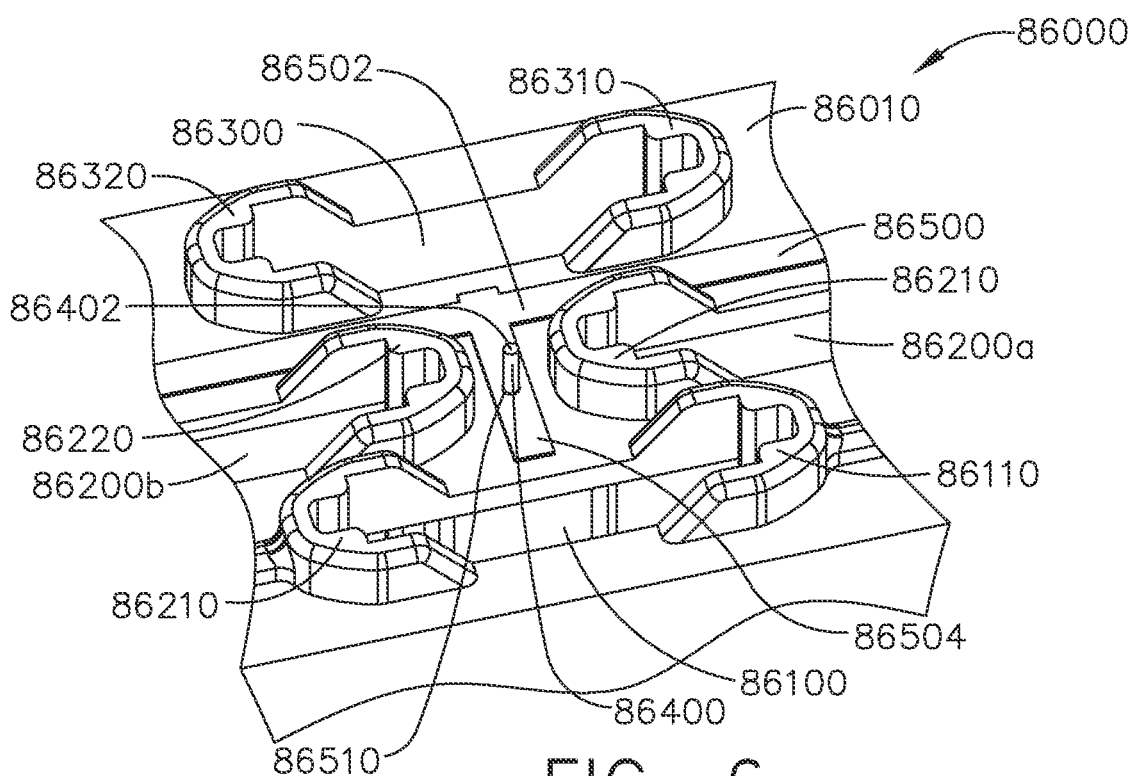
FIG. 6 is a partial perspective view of a deck surface comprising a trace retention feature in a first configuration.
Figure 7:
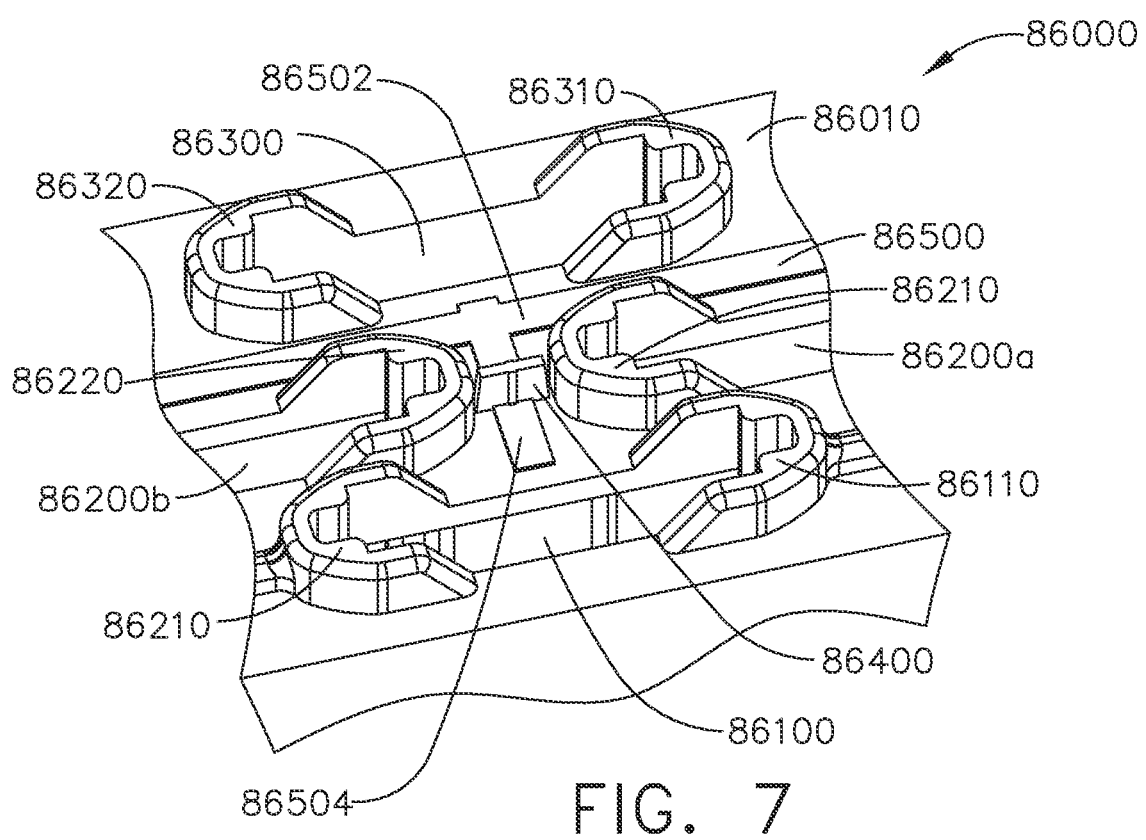
FIG. 7 is a partial perspective view of the deck surface of FIG. 6 with the trace retention feature in a second configuration.

Turning now to FIGS. 6 and 7, a staple cartridge 86000 similar in many respects to staple cartridge 85000 is depicted. The staple cartridge 86000 further comprises projections extending from the deck surface 86010. The projections are integrated, or integrally-formed, with the staple cartridge 86000 and extend away from the deck surface 86010. Multiple, discrete projections surround at least a portion of the staple cavities defined in the staple cartridge 86000. A first projection 86110 surrounds a proximal portion of a staple cavity 86100 in a first longitudinal row of staple cavities. A second projection 86120 surrounds a distal portion of the staple cavity 86100 from the first longitudinal row. A third projection 86210 surrounds a distal portion of a first staple cavity 86200a from a second longitudinal row of staple cavities, and a fourth projection 86220 surrounds a proximal portion of a second staple cavity 86200b from the second longitudinal row. A fifth projection 86310 surrounds a proximal portion of a staple cavity 86300 from a third longitudinal row of staple cavities, and a sixth projection 86320 surrounds a distal portion of the staple cavity 86300 from the third longitudinal row.

The projections extending from the deck surface 86010 define a valley, or recess, therebetween at least due to the longitudinally-offset orientation of the staple cavities 86200 in the second longitudinal row with respect to the staple cavities 86100, 86300 in the first and third longitudinal rows. The valley defines a continuous pathway extending between the staple cavities 86100, 86200, 86300 and their associated projections.

A flexible circuit 86500, similar in many respects to flexible circuit 85500, is configured to be secured against a deck surface 86010 of the staple cartridge 86000. The flexible circuit 86500 comprises a first portion 86502 configured to extend longitudinally along a deck surface of a staple cartridge. Stated another way, the first portion 86502 is configured to extend along the deck surface in between two longitudinal rows of staple cavities, such as in between the first longitudinal row and the second longitudinal row or in between the second longitudinal row and the third longitudinal row, for example. The first portion 86502 can be configured to extend along the deck surface in between the first longitudinal row of staple cavities and a longitudinal slot. The first portion 86502 can be configured to extend along the deck surface in between the third longitudinal row of staple cavities and an outer edge of the staple cartridge 86000.

The flexible circuit 86500 further comprises a second portion 86504 configured to extend laterally along the deck surface 86010. Stated another way, the second portion 86504 is configured to extend along the deck surface in between a staple cavity 86100 from the first longitudinal row and a longitudinally-aligned staple cavity 86300 from the third longitudinal row.

A through hole 86510, or aperture, is defined in the flexible circuit 86500. The through hole 86510 is sized to receive a trace retention feature 86400 of the staple cartridge 86000 therethrough. As shown in FIG. 6, the trace retention feature 86400 comprises a post extending from the deck surface 86010 in a first, unmelted, configuration. The trace retention feature 86400 can be integrally-formed with the staple cartridge 86000. While the through hole 86510 is shown as being defined in the second portion 86504 of the flexible circuit 86500, the through hole 86510 is also suitably defined in the first portion 86502 of the flexible circuit 86500, or wherever a corresponding trace retention feature is present.

The trace retention feature 86400 is comprised of a meltable material, such as a polymer, for example. In securing the flexible circuit 86500 against the deck surface 86010 of the staple cartridge 86000, the through hole 86510 of the flexible circuit 86500 is aligned with the trace retention feature 86400 of the staple cartridge 86000. Once desirably aligned, the trace retention feature 86400 is inserted through the through hole 86510 defined in the flexible circuit 86500. The post, or trace retention feature 86400 is then heated to a degree sufficient to melt an end 86402 of the trace retention feature 86400 into a second configuration as shown in FIG. 7. In its second configuration, the trace retention feature 86400 is no longer sized to easily and/or harmlessly move relative to the through hole 86510 defined in the flexible circuit 86500. A portion of the trace retention feature 86400 can be melted over an entire width of the flexible circuit 86500 and onto the surrounding, underlying deck surface 86010. In any event, the flexible circuit 86500 is secured against the deck surface 86010 when the trace retention feature 86400 is in its second, melted, configuration.

In addition to securing the trace retention feature 86400 to the staple cartridge 86000, the trace retention feature 86400 provides a tissue-gripping function. Tissue, or an adjunct layer, positioned against the deck surface 86010 is maintained in position generally by the clamping force exerted thereon by jaws of an end effector in a closed configuration and more locally by the projections 86110, 86120, 86210, 86220, 86310, 86320 extending from a cartridge deck surface 86010. If the staple cartridge 86000 comprises a post 86400 as a trace retention feature 86400, such post also interfaces with tissue, or an adjunct material, positioned there against. Melting the end 86402 of the post 86400 increases the overall surface area of the end 86402, and thus, increases the surface area of the interface between the post 86400 and adjacently-positioned tissue or adjunct material. An increased interface surface area allows for a desirably stronger gripping force to be exerted on the adjacent tissue or adjunct material.

As described with respect to the staple cartridge 85000 depicted in FIGS. 1-5, a continuous pathway defined by the flexible circuit 86500 can be elevated, or stepped, with respect to the deck surface 86010. Stated another way, areas of the staple cartridge 86000 along the path of the flexible circuit 86500 extend above the primary deck surface 86010 to a first height. While such first height is greater than zero (i.e., the height of the primary deck surface 86010), it is less than or equal to a height to which the projections extend from the primary deck surface 86010. Such an elevated pathway allows for the sensing array to achieve a better contact with an adjacent tissue and/or adjunct material than if such a pathway was the same height of the primary deck surface 86010, for example.

Figure 8:
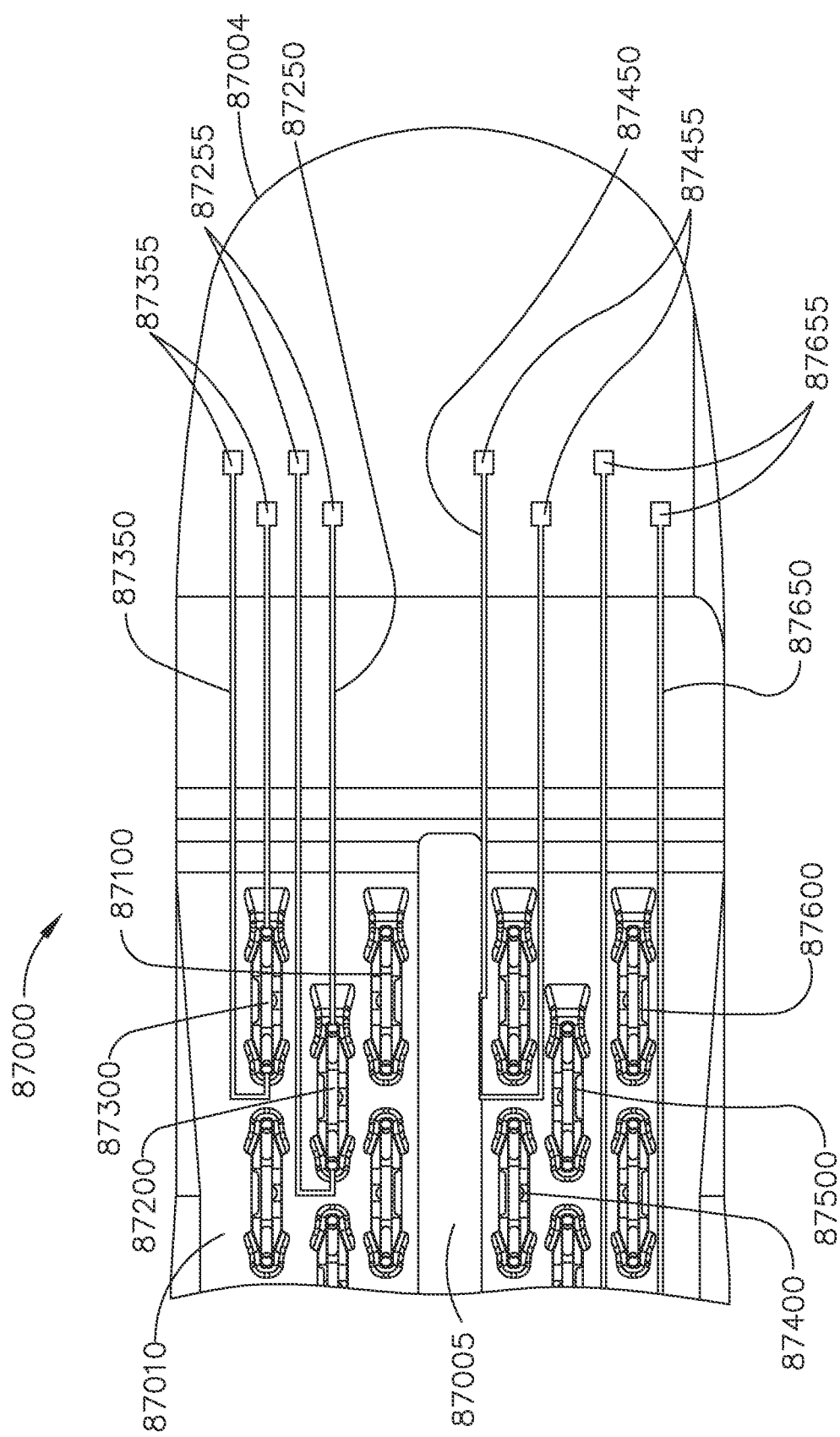
FIG. 8 is a partial plan view of a staple cartridge comprising electrical traces printed directly on a deck surface thereof.
Figure 9:
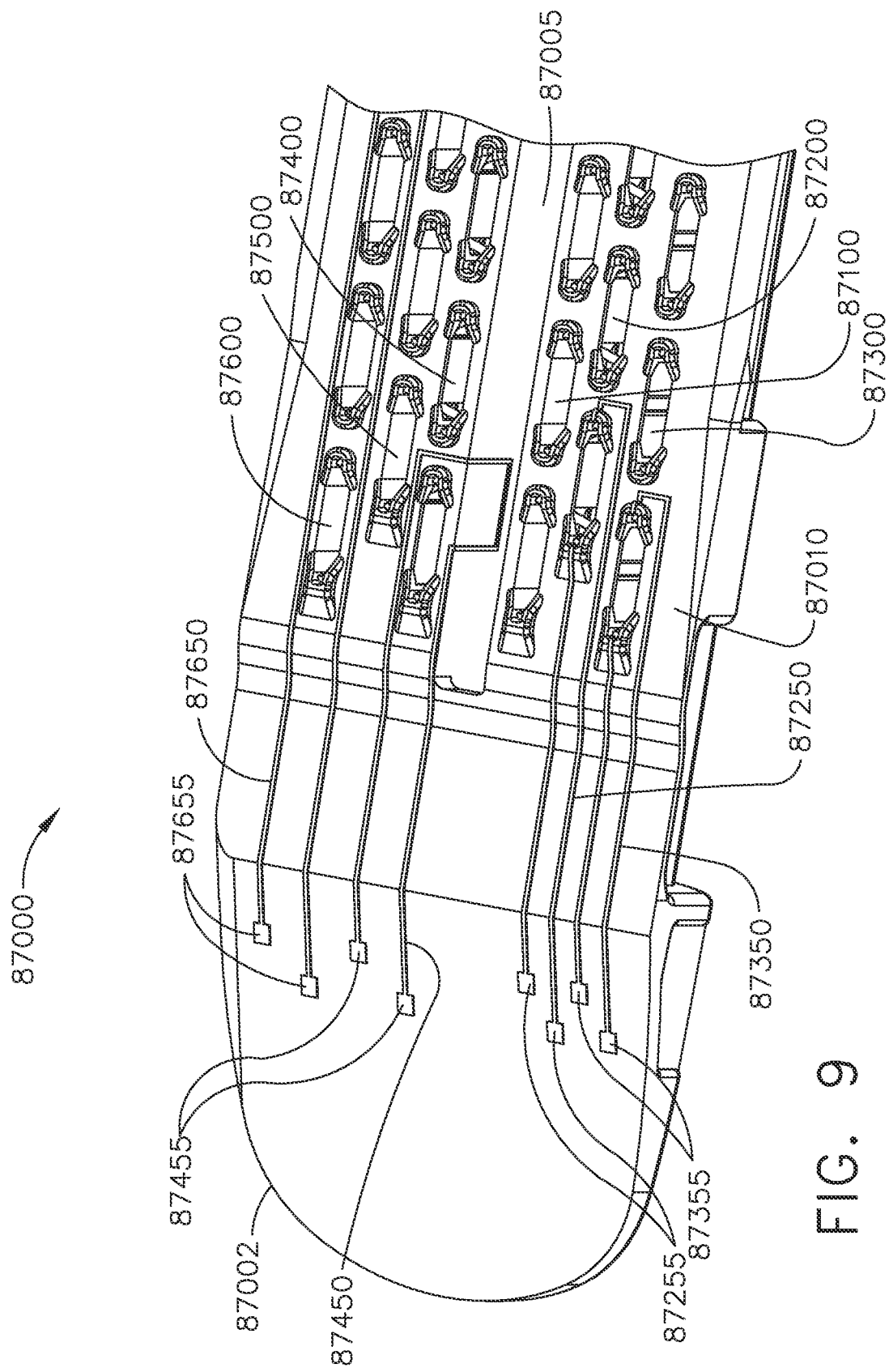
FIG. 9 is a partial perspective view of the staple cartridge of FIG. 8.

Referring now to FIGS. 8 and 9, a staple cartridge 87000 is depicted with electrical traces printed directly on the staple cartridge 87000. Such direct printing removes the need for a physical securement mechanism and allows for an unbounded sensing area. Staple cartridge 87000 is similar in many respects to staple cartridges 85000, 86000. The staple cartridge 87000 comprises a deck surface 87010 configured to oppose an anvil of the end effector when the staple cartridge 87000 is seated in a cartridge jaw. Staple cavities 87100, 87200, 87300, 87400, 87500, 87600 are defined in the staple cartridge 85000 and comprise staples movably stored therein. The staple cavities 87100, 87200, 87300, 87400, 87500, 87600 are arranged in six longitudinal rows, with three longitudinal rows on each side of a longitudinal slot 87005. The longitudinal rows of staple cavities extend between a proximal end and a distal end 87004 of the staple cartridge 87000. A first longitudinal row of staple cavities 87100 extends alongside a second longitudinal row of staple cavities 87200 on a first side of the longitudinal slot 87005. A third longitudinal row of staple cavities 87300 extends alongside the second longitudinal row of staple cavities 87300 on the first side of the longitudinal slot 87005. A fourth longitudinal row of staple cavities 87400 extends alongside a fifth longitudinal row of staple cavities 87500 on a second side of the longitudinal slot 87005. A sixth longitudinal row of staple cavities 87600 extends alongside the fifth longitudinal row of staple cavities 87500 on the second side of the longitudinal slot 87005. While six longitudinal rows of staple cavities are depicted as being defined in the staple cartridge 87000, any suitable number of staple cavity rows and/or staple cavities is envisioned and can be selected based on a particular surgical procedure, for example.

The longitudinal slot 87005 extends between the proximal end and the distal end 87004 of the staple cartridge 87000 and is sized to receive a sled driver, or firing actuator, to eject staples out of the staple cartridge 87000 during a staple firing stroke. Various aspects of staple cartridges are described in greater detail in U.S. Pat. No. 9,844,369, the disclosure of which is herein incorporated by reference in its entirety.

A first electrical trace 87250 is printed on the staple cartridge 87000 and wraps from a distal portion of the staple cartridge 87000 along the deck surface 87010 between the second longitudinal row of staple cavities 87200 and the third longitudinal row of staple cavities 87300. The first electrical trace 87250 continues directly into a distal-most staple cavity 87200 from the second longitudinal row and returns to the distal portion of the staple cartridge 87000. In addition to sensing a presence of tissue and/or an adjunct material against the deck surface 87010 in between longitudinal rows, extension of the first electrical trace 87250 into the staple cavity 87200 allows for the detection of a presence, or lack thereof, of a staple therein. If a staple is still detected within the staple cavity 87200, the surgical instrument and/or the user of the surgical instrument is aware that the staple firing stroke is incomplete. The first electrical trace 87250 comprises pads, or sensors, 87255 configured to detect a position of tissue and/or adjunct material along the deck surface 87010. Such feedback provides a user of the surgical instrument and/or the surgical instrument itself the ability to determine if repositioning of the surgical instrument is necessary, or desirable for an optimal outcome. While the pads 87255 are depicted as being at the terminal ends of the first electrical trace 87250, such pads 87255 can be positioned at any point and in any desired frequency along the first electrical trace 87250. While the first electrical trace 87250 is only depicted as extending into the distal-most staple cavity 87200 from the second longitudinal row of staple cavities, it is envisioned that the first electrical trace 87250 can extend into any suitable number of staple cavities from the second longitudinal row.

Similarly, a second electrical trace 87350 is printed on the staple cartridge 87000 and wraps from the distal portion of the staple cartridge 87000 along the deck surface 87010 between the third longitudinal row of staple cavities 87300 and an exterior edge of the staple cartridge 87000. The second electrical trace 87350 continues directly into a distal-most staple cavity 87300 from the third longitudinal row and returns to the distal portion of the staple cartridge 87000. The second electrical trace 87350 comprises pads, or sensors, 87355 configured to detect a position of tissue and/or adjunct material along the deck surface 87010. While the pads 87355 are depicted as being at the terminal ends of the second electrical trace 87350, such pads 87355 can be positioned at any point and in any desired frequency along the second electrical trace 87350. While the second electrical trace 87350 is only depicted as extending into the distal-most staple cavity 87300 from the third longitudinal row of staple cavities, it is envisioned that the second electrical trace 87350 can extend into any suitable number of staple cavities from the third longitudinal row.

A third electrical trace 87450 is printed on the staple cartridge 87000 and wraps from the distal portion of the staple cartridge 87000 along the deck surface 87010 between the fourth longitudinal row of staple cavities 87400 and the fifth longitudinal row of staple cavities 87500. Instead of returning to the distal portion of the staple cartridge 87000 through a staple cavity of the fourth row, the third electrical trace 87450 wraps back to the distal portion of the staple cartridge 87000 through the longitudinal slot 87005. In addition to sensing a presence of tissue and/or an adjunct material against the deck surface 87010 in between longitudinal rows, extension of the third electrical trace 87450 into the longitudinal slot 87005 allows for the detection of a firing actuator. The third electrical trace 87450 can extend into the longitudinal slot 87005 at a particular location so as to indicate a completion of the staple firing stroke when the firing actuator is detected at the particular location. The third electrical trace 87450 can extend into the longitudinal slot 87005 at an alternative and/or additional location(s) to detect the position of the firing actuator at any desired instant during the staple firing stroke. The third electrical trace 87450 comprises pads, or sensors, 87455 configured to detect a position of tissue and/or adjunct material along the deck surface 87010. While the pads 87455 are depicted as being at the terminal ends of the third electrical trace 87450, such pads 87455 can be positioned at any point and in any desired frequency along the third electrical trace 87450.

Similarly, a fourth electrical trace 87650 is printed on the staple cartridge 87000 and wraps from the distal portion of the staple cartridge 87000 along the deck surface 87010 between the sixth longitudinal row of staple cavities 87600 and an exterior edge of the staple cartridge 87000. The fourth electrical trace 87650 extends the entire length of the sixth longitudinal row of staple cavities 87600 and ultimately returns to the distal portion of the staple cartridge 87000 along the deck surface 87010 between the sixth longitudinal row of staple cavities 87600 and the fifth longitudinal row of staple cavities 87500. The fourth electrical trace 87650 comprises pads, or sensors, 87655 configured to detect a position of tissue and/or adjunct material along the deck surface 87010. While the pads 87655 are depicted as being at the terminal ends of the fourth electrical trace 87650, such pads 87655 can be positioned at any point and in any desired frequency along the fourth electrical trace 87650. For example, such pads 87655 can be placed every 10 mm along the length of the staple cartridge 87000.

While FIGS. 8 and 9 depict a single cartridge comprising four different electrical traces, it is envisioned that any combination of the depicted electrical traces can be used in any suitable longitudinal row and/or on any single staple cartridge.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10, 105, 142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled Surgical fastener applying apparatus, which published on Sep. 1, 2016, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/235,972, entitled MOTORIZED SURGICAL INSTRUMENT, now U.S. Pat. No. 9,050,083.
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Various aspects of the subject matter described herein are set out in the following examples.

1. A staple cartridge assembly for use with a surgical stapling instrument, wherein said staple cartridge assembly comprises a cartridge body (85000, 86000, 87000) comprising a deck (85010, 86010, 87010), a longitudinal slot (85005, 87005) extending from a proximal end (85002) toward a distal end (85004, 87004), a first longitudinal row of staple cavities (85100) defined in said deck alongside said longitudinal slot, wherein said first longitudinal row of staple cavities comprises a first staple cavity, a first projection (85110, 85120) extending from said deck, wherein said first projection surrounds at least a portion of said first staple cavity, a second longitudinal row of staple cavities (85200) defined in said deck, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity, a second projection (85210) extending from said deck, wherein said second projection surrounds at least a portion of said second staple cavity, a third projection (85220) extending from said deck, wherein said third projection surrounds at least a portion of said third staple cavity, an electrical trace (85500, 86500, 87250, 87350, 87450, 87650) extending across said deck along a trace pathway, wherein said trace pathway extends laterally and longitudinally across said deck between said first projection, said second projection, and said third projection, and a trace retention feature (85150, 85350, 86400) configured to retain said electrical trace against said deck.
2. The staple cartridge assembly of Example 1, wherein said trace retention feature comprises a post (86400) extending from said deck between said second projection and said third projection.
3. The staple cartridge assembly of any one of Examples 1 or 2, wherein said trace retention feature is integrally formed with said cartridge body.
4. The staple cartridge assembly of any one of Examples 1, 2, or 3, further comprising a flexible circuit board (85500, 86500), and wherein said electrical trace is printed on said flexible circuit board.
5. The staple cartridge assembly of Example 4, wherein said flexible circuit board comprises an aperture (86510) defined therein, and wherein said trace retention feature is configured to extend through said aperture.
6. The staple cartridge assembly of Example 5, wherein said trace retention feature extends from said deck to a first end (86402), wherein when said trace retention feature extends through said opening of said flexible circuit board, said first end is configured to be melted to secure said flexible circuit board against said deck.
7. The staple cartridge assembly of Example 6, wherein said first end comprises a tissue-facing surface (86402), wherein said tissue-facing surface comprises a first surface area prior to said first end being melted, wherein said tissue-facing surface comprises a second surface area after said first end is melted, wherein said second surface area is greater than said first surface area.
8. The staple cartridge assembly of any one of Examples 1, 2, 3, 4, 5, 6, or 7, wherein said trace pathway longitudinally extends between said first longitudinal row of staple cavities and said second longitudinal row of staple cavities, and wherein said trace pathway laterally extends between said second projection and said third projection.
9. The staple cartridge assembly of any one of Examples 1, 2, 3, 4, 5, 6, 7, or 8, wherein said trace pathway is continuous.
10. The staple cartridge assembly of any one of Examples 4, 5, 6, or 7, wherein said trace retention feature comprises a relief slot (85150) defined in said cartridge body, wherein said relief slot extends into said first staple cavity, and wherein said flexible circuit board comprises an attachment member (85510) sized to be received in said relief slot to retain said flexible circuit board against said deck in a desired orientation.
11. The staple cartridge assembly of any one of Examples 1, 2, 3, 4, 5, 6, 7, 8, 9, or 10, wherein said deck comprises a base surface and a trace-supporting surface, wherein said trace-supporting surface is stepped relative to said base surface, wherein said electrical trace extends along said trace-supporting surface.
12. The staple cartridge assembly of Example 11, wherein said first projection extends from said deck to a first height, wherein said second projection extends from said deck to a second height, wherein said third projection extends from said deck to a third height, wherein said trace-supporting surface is stepped to a fourth height relative to said base surface, and wherein said fourth height is less than said first height, said second height, and said third height.
13. The staple cartridge assembly of any one of Examples 1, 2, 3, 4, 5, 6, 7, 8, 9, 10, 11, or 12, wherein said electrical trace comprises a sensing array configured to detect a presence of tissue along a longitudinal dimension of said cartridge body.
14. The staple cartridge assembly of Example 13, wherein said sensing array is configured to detect a presence of tissue at a first location of said cartridge body and a second location of said cartridge body, and wherein said second location is distal to said first location.
15. The staple cartridge assembly of any one of Examples 1, 2, 3, 4, 5, 6, 7, 8, 9, 10, 11, 12, 13, or 14, wherein said electrical trace is printed directly onto said deck.
16. A staple cartridge assembly for use with a surgical stapling instrument, wherein said staple cartridge assembly comprises a cartridge body comprising a deck, a longitudinal slot extending from a proximal end toward a distal end, a first longitudinal row of staple cavities defined in said deck alongside said longitudinal slot, wherein said first longitudinal row of staple cavities comprises a first staple cavity, a first projection extending from said deck, wherein said first projection surrounds at least a portion of said first staple cavity, a second longitudinal row of staple cavities defined in said deck, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity, a second projection extending from said deck, wherein said second projection surrounds at least a portion of said second staple cavity, and a third projection extending from said deck, wherein said third projection surrounds at least a portion of said third staple cavity. The staple cartridge further comprises an electrical trace extending across said deck along a trace pathway, wherein said trace pathway extends laterally and longitudinally across said deck between said first projection, said second projection, and said third projection and a trace retention feature configured to retain said electrical trace against said deck.
17. The staple cartridge assembly of Example 16, wherein said trace retention feature comprises a post extending from said deck between said second projection and said third projection.

18. The staple cartridge assembly of Example 16, wherein said trace retention feature is integrally formed with said cartridge body.
19. The staple cartridge assembly of Example 16, further comprising a flexible circuit board, and wherein said electrical trace is printed on said flexible circuit board.
20. The staple cartridge assembly of Example 19, wherein said flexible circuit board comprises an aperture defined therein, and wherein said trace retention feature is configured to extend through said aperture.
21. The staple cartridge assembly of Example 20, wherein said trace retention feature extends from said deck to a first end, wherein when said trace retention feature extends through said opening of said flexible circuit board, said first end is configured to be melted to secure said flexible circuit board against said deck.
22. The staple cartridge assembly of Example 21, wherein said first end comprises a tissue-facing surface, wherein said tissue-facing surface comprises a first surface area prior to said first end being melted, wherein said tissue-facing surface comprises a second surface area after said first end is melted, wherein said second surface area is greater than said first surface area.
23. The staple cartridge assembly of Example 21, wherein said trace pathway longitudinally extends between said first longitudinal row of staple cavities and said second longitudinal row of staple cavities, and wherein said trace pathway laterally extends between said second projection and said third projection.
24. The staple cartridge assembly of Example 21, wherein said trace pathway is continuous.
25. The staple cartridge assembly of Example 21, wherein said trace retention feature comprises a relief slot defined in said cartridge body, wherein said relief slot extends into said first staple cavity, and wherein said flexible circuit board comprises an attachment member sized to be received in said relief slot to retain said flexible circuit board against said deck in a desired orientation.
26. The staple cartridge assembly of Example 21, wherein said deck comprises a base surface and a trace-supporting surface, wherein said trace-supporting surface is stepped relative to said base surface, wherein said electrical trace extends along said trace-supporting surface.
27. The staple cartridge assembly of Example 26, wherein said first projection extends from said deck to a first height, wherein said second projection extends from said deck to a second height, wherein said third projection extends from said deck to a third height, wherein said trace-supporting surface is stepped to a fourth height relative to said base surface, and wherein said fourth height is less than said first height, said second height, and said third height.
28. The staple cartridge assembly of Example 16, wherein said electrical trace comprises a sensing array configured to detect a presence of tissue along a longitudinal dimension of said cartridge body.
29. The staple cartridge assembly of Example 28, wherein said sensing array is configured to detect a presence of tissue at a first location of said cartridge body and a second location of said cartridge body, and wherein said second location is distal to said first location.
30. The staple cartridge assembly of Example 16, wherein said electrical trace is printed directly onto said deck.
31. A staple cartridge assembly for use with a surgical stapling instrument, wherein said staple cartridge assembly comprises a cartridge body comprising a deck, a proximal end, a distal end, a longitudinal slot extending from said proximal end toward said distal end, a first longitudinal row of staple cavities defined in said deck, wherein said first longitudinal row of staple cavities is positioned laterally with respect to said longitudinal slot, and wherein said first longitudinal row of staple cavities comprises a first staple cavity, a first projection extending from said deck, wherein said first projection surrounds at least a portion of said first staple cavity, a second longitudinal row of staple cavities defined in said deck, wherein said second longitudinal row of staple cavities is positioned laterally with respect to said first longitudinal row of staple cavities, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity, a second projection extending from said deck, wherein said second projection surrounds at least a portion of said second staple cavity, and a third projection extending from said deck, wherein said third projection surrounds at least a portion of said third staple cavity. The staple cartridge assembly further comprises a conductor extending across said deck along a trace pathway, wherein said conductor extends laterally and longitudinally across said deck between said first projection, said second projection, and said third projection, a trace retainer, wherein said conductor is attached to said cartridge body by said trace retainer, and staples removably stored in said first longitudinal row of staple cavities and said second longitudinal row of staple cavities.
32. A staple cartridge assembly for use with a surgical stapling instrument, wherein said staple cartridge assembly comprises a cartridge body comprising a deck, a proximal end, a distal end, a longitudinal slot extending from said proximal end toward said distal end, a first longitudinal row of staple cavities defined in said deck, wherein said first longitudinal row of staple cavities is positioned laterally with respect to said longitudinal slot, and wherein said first longitudinal row of staple cavities comprises a first staple cavity, a first cavity extender extending from said deck, wherein said first cavity extender surrounds at least a portion of said first staple cavity, a second longitudinal row of staple cavities defined in said deck, wherein said second longitudinal row of staple cavities is positioned laterally with respect to said first longitudinal row of staple cavities, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity, a second cavity extender extending from said deck, wherein said second cavity extender surrounds at least a portion of said second staple cavity, and a third cavity extender extending from said deck, wherein said third cavity extender surrounds at least a portion of said third staple cavity. The staple cartridge assembly further comprises a trace extending across said deck along a trace pathway, wherein said trace pathway extends laterally and longitudinally across said deck from said first cavity extender to said second cavity extender and said third cavity extender and staples removably stored in said first longitudinal row of staple cavities and said second longitudinal row of staple cavities.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A staple cartridge assembly for use with a surgical stapling instrument, wherein said staple cartridge assembly comprises:
   a cartridge body comprising a deck;
   a longitudinal slot extending from a proximal end toward a distal end;
   a first longitudinal row of staple cavities defined in said deck alongside said longitudinal slot, wherein said first longitudinal row of staple cavities comprises a first staple cavity;
   a first projection extending from said deck, wherein said first projection surrounds at least a portion of said first staple cavity;
   a second longitudinal row of staple cavities defined in said deck, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity;
   a second projection extending from said deck, wherein said second projection surrounds at least a portion of said second staple cavity;
   a third projection extending from said deck, wherein said third projection surrounds at least a portion of said third staple cavity;
   an electrical trace extending across said deck along a trace pathway, wherein said trace pathway extends laterally and longitudinally across said deck between said first projection, said second projection, and said third projection; and
   a post extending from said deck and configured to retain said electrical trace against said deck.

2. The staple cartridge assembly of claim 1, wherein said post extends from said deck between said second projection and said third projection.

3. The staple cartridge assembly of claim 1, wherein said post is integrally formed with said cartridge body.

4. The staple cartridge assembly of claim 1, further comprising a flexible circuit board, and wherein said electrical trace is printed on said flexible circuit board.

5. The staple cartridge assembly of claim 1, wherein said trace pathway longitudinally extends between said first longitudinal row of staple cavities and said second longitudinal row of staple cavities, and wherein said trace pathway laterally extends between said second projection and said third projection.

6. The staple cartridge assembly of claim 1, wherein said trace pathway is continuous.

7. The staple cartridge assembly of claim 1, wherein said electrical trace comprises a sensing array configured to detect a presence of tissue along a longitudinal dimension of said cartridge body.

8. The staple cartridge assembly of claim 7, wherein said sensing array is configured to detect a presence of tissue at a first location of said cartridge body and a second location of said cartridge body, and wherein said second location is distal to said first location.

9. A staple cartridge assembly for use with a surgical stapling instrument, wherein said staple cartridge assembly comprises:
   a cartridge body comprising a deck;
   a longitudinal slot extending from a proximal end toward a distal end;
   a first longitudinal row of staple cavities defined in said deck alongside said longitudinal slot, wherein said first longitudinal row of staple cavities comprises a first staple cavity;
   a first projection extending from said deck, wherein said first projection surrounds at least a portion of said first staple cavity;

a second longitudinal row of staple cavities defined in said deck, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity;
a second projection extending from said deck, wherein said second projection surrounds at least a portion of said second staple cavity;
a third projection extending from said deck, wherein said third projection surrounds at least a portion of said third staple cavity;
an electrical trace extending across said deck along a trace pathway, wherein said trace pathway extends laterally and longitudinally across said deck between said first projection, said second projection, and said third projection, and wherein said trace is printed on a flexible circuit board; and
a trace retainer configured to retain said electrical trace against said deck, wherein said flexible circuit board comprises an aperture defined therein, and wherein said trace retainer is configured to extend through said aperture.

10. The staple cartridge assembly of claim 9, wherein said trace retainer extends from said deck to a first end, wherein when said trace retainer extends through said opening of said flexible circuit board, said first end is configured to be melted to secure said flexible circuit board against said deck.

11. The staple cartridge assembly of claim 10, wherein said first end comprises a tissue-facing surface, wherein said tissue-facing surface comprises a first surface area prior to said first end being melted, wherein said tissue-facing surface comprises a second surface area after said first end is melted, wherein said second surface area is greater than said first surface area.

12. A staple cartridge assembly for use with a surgical stapling instrument, wherein said staple cartridge assembly comprises:
a cartridge body, comprising:
a deck;
a proximal end;
a distal end;
a longitudinal slot extending from said proximal end toward said distal end;
a first longitudinal row of staple cavities defined in said deck, wherein said first longitudinal row of staple cavities is positioned laterally with respect to said longitudinal slot, and wherein said first longitudinal row of staple cavities comprises a first staple cavity;
a first projection extending from said deck, wherein said first projection surrounds at least a portion of said first staple cavity;
a second longitudinal row of staple cavities defined in said deck, wherein said second longitudinal row of staple cavities is positioned laterally with respect to said first longitudinal row of staple cavities, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity;
a second projection extending from said deck, wherein said second projection surrounds at least a portion of said second staple cavity;
a third projection extending from said deck, wherein said third projection surrounds at least a portion of said third staple cavity; and
a relief slot defined in said cartridge body, wherein said relief slot extends into said first staple cavity;
a flexible circuit comprising a conductor extending across said deck along a trace pathway, wherein said conductor extends laterally and longitudinally across said deck between said first projection, said second projection, and said third projection, and wherein a portion of said flexible circuit is sized to be received in said relief slot to retain said flexible circuit against said deck in a desired orientation; and
staples removably stored in said first longitudinal row of staple cavities and said second longitudinal row of staple cavities.

13. The staple cartridge assembly of claim 12, wherein said flexible circuit comprises a sensor configured to detect a presence of tissue.

14. The staple cartridge assembly of claim 12, wherein said trace pathway longitudinally extends between said first longitudinal row of staple cavities and said second longitudinal row of staple cavities, and wherein said trace pathway laterally extends between said second projection and said third projection.

15. The staple cartridge assembly of claim 12, wherein said cartridge body comprises a fourth staple cavity defined in said deck, and wherein said relief slot extends into said fourth staple cavity.

16. The staple cartridge assembly of claim 12, wherein said portion of said flexible circuit is sized to be received in said relief slot comprises a T-shaped end sized to be received in said relief slot.

17. A staple cartridge assembly for use with a surgical stapling instrument, wherein said staple cartridge assembly comprises:
a cartridge body, comprising:
a deck comprising a base surface and a trace-supporting surface, wherein said trace-supporting surface is stepped relative to said base surface;
a proximal end;
a distal end;
a longitudinal slot extending from said proximal end toward said distal end;
a first longitudinal row of staple cavities defined in said deck, wherein said first longitudinal row of staple cavities is positioned laterally with respect to said longitudinal slot, and wherein said first longitudinal row of staple cavities comprises a first staple cavity;
a first cavity extender extending from said deck, wherein said first cavity extender surrounds at least a portion of said first staple cavity;
a second longitudinal row of staple cavities defined in said deck, wherein said second longitudinal row of staple cavities is positioned laterally with respect to said first longitudinal row of staple cavities, wherein said second longitudinal row of staple cavities comprises a second staple cavity and a third staple cavity, wherein a proximal end of said second staple cavity is proximal to a proximal end of said first staple cavity, and wherein said third staple cavity is distal to said second staple cavity;
a second cavity extender extending from said deck, wherein said second cavity extender surrounds at least a portion of said second staple cavity; and a third cavity extender extending from said deck, wherein said third cavity extender surrounds at least a portion of said third staple cavity;

a trace extending across said deck along a trace pathway on said trace-supporting surface, wherein said trace pathway extends laterally and longitudinally across said deck from said first cavity extender to said second cavity extender and said third cavity extender; and staples removably stored in said first longitudinal row of staple cavities and said second longitudinal row of staple cavities.

18. The staple cartridge assembly of claim 17, wherein said first cavity extender extends from said deck to a first height, wherein said second cavity extender extends from said deck to a second height, wherein said third cavity extender extends from said deck to a third height, wherein said trace-supporting surface is stepped to a fourth height relative to said base surface, and wherein said fourth height is less than said first height, said second height, and said third height.

19. The staple cartridge assembly of claim 17, wherein said trace is printed directly onto said deck.

20. The staple cartridge assembly of claim 17, wherein said trace comprises a sensor configured to detect a presence of tissue.

* * * * *